United States Patent
Gaillard et al.

(10) Patent No.: US 7,314,878 B2
(45) Date of Patent: Jan. 1, 2008

(54) PIPERAZINE BENZOTHIAZOLES AS AGENTS FOR THE TREATMENT OF CEREBRAL ISCHEMIC DISORDERS OR CNS DISORDERS

(75) Inventors: Pascale Gaillard, St. Julien-en-Genevois (FR); Jean-Pierre Gotteland, Beaumont (FR); Pierre-Alain Vitte, Cranves-Sales (FR)

(73) Assignee: Laboratories Serono SA, Vaud (CH)

( * ) Notice: Subject to any disclaimer, the term of this patent is extended or adjusted under 35 U.S.C. 154(b) by 59 days.

(21) Appl. No.: 10/511,438

(22) PCT Filed: Apr. 25, 2003

(86) PCT No.: PCT/EP03/04323

§ 371 (c)(1),
(2), (4) Date: Jun. 10, 2005

(87) PCT Pub. No.: WO03/091249

PCT Pub. Date: Nov. 6, 2003

(65) Prior Publication Data
US 2005/0261304 A1 Nov. 24, 2005

(30) Foreign Application Priority Data
Apr. 25, 2002 (EP) .................... 02100417

(51) Int. Cl.
C07D 417/06 (2006.01)
C07D 417/14 (2006.01)
A61K 31/506 (2006.01)

(52) U.S. Cl. ................... 514/252.14; 544/295
(58) Field of Classification Search ............ 544/295; 514/252.14
See application file for complete search history.

(56) References Cited

U.S. PATENT DOCUMENTS
2005/0261304 A1 11/2005 Gaillard et al.

FOREIGN PATENT DOCUMENTS
| JP | 11-080155 | 3/1999 |
| WO | 01/47920 | 7/2001 |
| WO | 02/26711 | 4/2002 |

OTHER PUBLICATIONS

Sah et al., Translation Inhibitors Sensitize Prostate Cancer Cells to Apoptosis Induced by Tumor Necrosis Factor-related Apoptosis-inducing Ligand (TRAIL) by Activating c-Jun N-terminal Kinase, The Journal of Biological Chemistry, vol. 278, No. 23, pp. 20593-26002, Jun. 2003.*
Layzer, Degenerative Diseases of the Nervous System, Cecil Textbook of Medicine, 20th Edition, vol. 2, pp. 2050-2057, 1996.*
Damasio, Alzheimer's Disease and Related Dementias, Cecil Textbook of Medicine, 20th Edition, vol. 2, pp. 1992-1996, 1996.*
Roger J. Davis, "Signal transduction by the JNK group of MAP kinases", CELL, vol. 103, pp. 239-252 Oct. 13, 2000.
Shashi Gupta, et al., "Selective interaction of JNK protein kinase isoforms with transcription factors", The EMBO Journal, vol. 15, No. 11, pp. 2760-2770 1996.
Calin D. Dumitru, et al., "TNF-α induction by LPS is regulated posttranscriptionally via a Tpl2/ERK-dependent pathway", CELL, vol. 103, pp. 1071-1083 Dec. 22, 2000.
Zuoning Han, et al., "c-Jun N-terminal kinase is required for metalloproteinase expression and joint destruction in inflammatory arthritis", The Journal of Clinical Investigation, vol. 108, No. 1, pp. 73-81, 2001.
Hiroshi Nishina, et al., "Impaired CD28-mediated interleukin 2 production and proliferation in stress kinase SAPK/ERK1 kinase (SEK1)/mitogen-activated protein kinase kinase 4(MKK4)-deficient T lymphocytes", The Journal of Experimental Medicine, vol. 186, No. 6, pp. 941-953 Sep. 15, 1997.
Stephan J. Kempiak, et al., "the jun kinase cascade is responsible for activating the CD28 response element of the IL-2 promoter: proof of cross-talk with the IκB kinase cascade", The Journal of Immunology, vol. 162, pp. 3176-3187 1999.
S. M. de la Monte, et al., "Oxygen free radical injury is sufficient to cause some Alzheimer-type molecular abnormalities in human CNS neuronal cells", Journal of Alzheimer's Disease, vol. 2, pp. 261-281 2000.
Xiongwei Zhu, et al., "Activation and redistribution of c-Jun N-terminal kinase/stress activated protein kinase in degenerating neurons in Alzheimer's disease", Journal of Neurochemistry, vol. 76, pp. 435-441 2001.
Li Xu, et al., "Assess the in vivo activation of signal transduction pathways with pathdetect reporting systems", STRATEGIES, vol. 11, pp. 94-97 2001.
Mausumee Guha, et al., "LPS induction of gene expression in human monocytes", Cellular Signalling, vol. 13, pp. 85-94 2001.
A. Jackie Hunter, et al., "Animal models of acute ischaemic stroke: can they predict clinically successful neuroprotective drugs", TIPS, vol. 16, pp. 123-128 1995.
F. Block, "Global ischemia and behavioural deficits", Progress in Neurobiology, vol. 58, pp. 279-295 1999.
Susan C. Gerhardt, et al., "Motor activity changes following cerebral ischemia in gerbils are correlated with the degree of neuronal degeneration in hippocampus", Behavioral Neuroscience, vol. 102, No. 2, pp. 301-303 1988.
A. Lorris Betz, et al., "Blood-brain-cerebrospinal fluid barriers", Basic Neurochemistry: Molecular, Cellular, and Medical Aspects, 5th edition, chapter 32, pp. 681-699, 1994.
Gary W. Goldstein, et al., "The blood-brain barrier", Scientific American, pp. 70-79 Sep. 1986.
U.S. Appl. No. 10/571,291, filed Mar. 9, 2006, Gaillard, et al.

* cited by examiner

Primary Examiner—Deepak Rao
(74) Attorney, Agent, or Firm—Oblon, Spivak, McClelland, Maier & Neustadt, P.C.

(57) ABSTRACT

The present invention is related to piperazine henzothiazole derivatives, notably for use in the treatment and/or prophylaxis of cerebral ischemic disorders or CNS disorders. The present invention is furthermore related to methods of their preparation.

9 Claims, No Drawings

PIPERAZINE BENZOTHIAZOLES AS AGENTS FOR THE TREATMENT OF CEREBRAL ISCHEMIC DISORDERS OR CNS DISORDERS

This application is a 371 of PCT/EP03/04323 filed Apr. 25, 2003.

FIELD OF THE INVENTION

The present invention is related to piperazine benzothiazole derivatives, notably for use in the treatment and/or prophylaxis of cerebral ischemic disorders or CNS disorders. The present invention is furthermore related to methods of their preparation.

BACKGROUND OF THE INVENTION

Mammalian cells respond to some extracellular stimuli by activating signaling cascades which are mediated by various mitogen-activated protein kinases (MAPKs). Despite the differences in their response to upstream stimuli, the MAP kinase cascades are organized in a similar fashion, consisting of MAP kinase kinase kinases (MAPKKK or MEKK), MAP kinase kinases (MAPKK or MKK) and MAP kinases (MAPK). MAP kinases are a-broad family of kinases which includes c-Jun N-Terminal kinases (JNKs), also known as "stress-activated protein kinases" (SAPKs), as well as extracellular signal regulated kinases (ERKs) and p38 MAP kinases. Each of these three MAP kinases sub-families is involved in at least three different but parallel pathways conveying the information triggered by external stimuli. The JNK signaling pathway is activated by exposure of cells to environmental stress—such as chemical toxins, radiation, hypoxia and osmotic shock—as well as by treatment of cells with growth factors or pro-inflammatory cytokines—such as tumour necrosis factor alpha (TNF-α) or interleukin-1 beta (IL-1β).

Two MAP kinase kinases (known as MKKs or MAP-KKs), i.e. MKK4 (known also as JNKK1) and MKK7, activate JNK by a dual phosphorylation of specific threonine and tyrosine residues located within a Thr-Pro-Tyr motif on the activation loop on the enzyme, in response to cytokines and stress signals. Even further upstream in the signaling cascade, MKK4 is known to be activated itself also by a MAP kinase kinase kinase, MEKK1 through phosphorylation at serine and threonine residues.

Once activated, JNK binds to the N-terminal region of transcription factor targets and phosphorylates the transcriptional activation domains resulting in the up-regulation of expression of various gene products, which can lead to apoptosis, inflammatory responses or oncogenic processes (1).

Some transcription factors known to be JNK substrates are the Jun proteins (c-jun, JunB and Jun D), the related transcription factors ATF2 and ATFa, Ets transcription factors such as Elk-1 and Sap-1, the tumor suppressor p53 and a cell death domain protein (DENN).

Three distinct JNK enzymes have been identified as products of the genes JNK1, JNK2 and JNK3 and ten different isoforms of JNK have been identified (2). JNK1 and −2 are ubiquitously expressed in human tissues, whereas JNK3 is selectively expressed in the brain, heart and testes (2). Each isoform binds to the substrates with different affinities, suggesting, in vivo, a substrate specific regulation of the signaling pathways by the different JNK isoforms.

Activation of the JNK pathway has been documented in a number of disease processes, thus providing a rationale for targeting this pathway for drug discovery. In addition, molecular genetic approaches have validated the pathogenic role of this pathway in several diseases.

For example, auto-immune and inflammatory diseases derive from the inappropriate activation of the immune system. Activated immune cells express many genes encoding inflammatory molecules, including cytokines, growth factors, cell surface receptors, cell adhesion molecules and degradative enzymes. Many of these genes are known to be regulated by the JNK pathway, through the activation of the transcription factors c-Jun and ATF-2.

The inhibition of JNK activation in bacterial lipopolysaccharide-stimulated macrophages, effectively modulates the production of the key pro-inflammatory cytokine, TNFα (3).

The inhibition of JNK activation decreases the transcription factor activation responsible of the inducible expression of matrix metalloproteinases (MMPs) (4), which are known to be responsible of the promotion of cartilage and bone erosion in rheumatoid arthritis and of generalized tissue destruction in other auto-immune diseases.

The JNK cascade is also activated in T cells by antigen stimulation and CD28 receptor co-stimulation (5) and regulates the production of the IL-2 promoter (6). Inappropriate activation of T lymphocytes initiates and perpetuates many auto-immune diseases, including asthma, inflammatory bowel syndrome and multiple sclerosis.

In neurons vulnerable to damage from Alzheimer's disease and in CA1 neurons of patients with acute hypoxia (7), JNK3 protein is highly expressed. The JNK3 gene was also found, to be expressed in the damaged regions of the brains of Alzheimer's patients (8). In addition, neurons from JNK3 KO mice were found to become resistant to kainic acid induced neuronal apoptosis compared to neurons from wild-type mice.

Based on these findings, the JNK signaling pathway and especially that of JNK2 and JNK3, is thought to be implicated in apoptosis-driven neurodegenerative diseases such as Alzheimer's disease, Parkinson's disease, epilepsy and seizures, Huntington's disease, CNS disorders, traumatic brain injuries as well as ischemic disorders and hemorrhaging strokes.

Several small molecules have been proposed as modulators of the JNK pathway (WO 00/35909; WO 00/35906; WO 00/3592, WO 00/64872, WO 01/12609, WO 00/75118, WO 01/12621).

WO 01/47920 discloses benzothiazole derivatives as JNK inhibitors of formula (A).

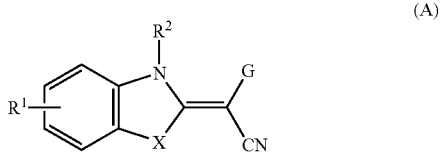

(A)

A general problem in the treatment of CNS disorders, e.g. cerebral disorders, is the transport of the therapeutic compounds into the CNS system, e.g. to the brain. It is well known that the BBB impedes the delivery of drugs to the CNS.

The Blood-Brain Barrier (BBB) is a barrier, made up of capillary walls and surrounding neuroglia, that limits the passages of substances between the blood and brain tissue.

The Blood-Brain Barrier (BBB) maintains a homeostatic environment in the central nervous system (CNS). The capillaries that supply the blood to the brain have tight junctions which block passage of most molecules through the capillary endothelial membranes. While the membranes do allow passage of lipid soluble materials, such as heroin and other psychoactive drugs, water soluble materials such as glucose, proteins and amino acids do not pass through the BBB. Mediated transport mechanisms exist to transport-glucose and essential amino acids across the BBB. Active transport mechanisms remove molecules which become in excess, such as potassium, from the brain. For a general review see Goldstein and Betz, 1986 and Betz et al, 1994, incorporated herein in their entirety by reference (14; 15).

SUMMARY OF THE INVENTION

The present invention is related to piperazine benzothiazole derivatives, notably for use in the treatment and/or prophylaxis of cerebral ischemic disorders or CNS disorders. The present invention is furthermore related to methods of their preparation.

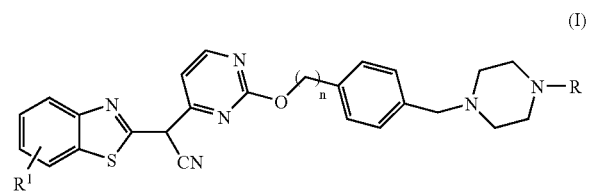

(I)

DESCRIPTION OF THE INVENTION

The following paragraphs provide definitions of the various chemical moieties that make up the compounds according to the invention and are intended to apply uniformly throughout the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g., phenyl) or multiple condensed rings (e.g. naphthyl). Preferred aryl include phenyl, naphthyl, phenantrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

"$C_2$-$C_6$-alkenyl aryl" refers to $C_2$-$C_6$-alkenyl groups having an aryl substituent, including 2-phenylvinyl and the like.

"$C_2$-$C_6$-alkenyl heteroaryl" refers to $C_2$-$C_6$-alkenyl groups having a heteroaryl substituent, including 2-(3-pyridinyl)vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"$C_2$-$C_6$-alkynyl aryl" refers to $C_2$-$C_6$-alkynyl groups having an aryl substituent, including phenylethynyl and the like.

"$C_2$-$C_6$-alkynyl heteroaryl" refers to $C_2$-$C_6$-alkynyl groups having a heteroaryl substituent, including 2-thienylethynyl and the like.

"$C_3$-$C_8$-cycloalkyl" refers to a saturated carbocyclic group of from 3 to 8 carbon atoms having a single ring (e.g, cyclohexyl) or multiple condensed rings (e.g. norbornyl). Preferred cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Preferred heterocycloalkyl include pyrrolidine, piperidine, piperazine, 1-methylpiperazine, morpholine, and the like.

"$C_1$-$C_6$-alkyl cycloalkyl" refers to $C_1$-$C_6$-alkyl groups having a cycloalkyl substituent, including cyclohexylmethyl, cyclopentylpropyl, and the like.

"$C_1$-$C_6$-alkyl heterocycloalkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

"Carboxy" refers to the group —C(O)OH.

"$C_1$-$C_6$-alkyl carboxy" refers to $C_1$-$C_5$-alkyl groups having an carboxy substituent, including 2-carboxyethyl and the like.

"Acyl" refers to the group —C(O)R where R includes "$C_1$-$C_6$-alkyl", "aryl", "heteroaryl", "$C_1$-$C_6$-alkyl aryl" or "$C_1$-$C_6$-alkyl heteroaryl".

"$C_1$-$C_6$-alkyl acyl" refers to $C_1$-$C_6$-alkyl groups having an acyl substituent, including 2-acetylethyl and the like.

"Acyloxy" refers to the group —OC(O)R where R includes "$C_1$-$C_6$-alkyl", "aryl", "hetero-aryl", "$C_1$-$C_6$-alkyl aryl" or "$C_1$-$C_6$-alkyl heteroaryl".

"$C_1$-$C_6$-alkyl acyloxy" refers to $C_1$-$C_6$-alkyl groups having an acyloxy substituent, including 2-(acetyloxy)ethyl and the like.

"Alkoxy" refers to the group —O—R where R includes "$C_1$-$C_6$-alkyl" or "aryl" or "hetero-aryl" or "$C_1$-$C_6$-alkyl" or "$C_1$-$C_6$-alkyl heteroaryl". Preferred alkoxy groups include by way of example, methoxy, ethoxy, phenoxy and the like.

"$C_1$-$C_6$-alkyl alkoxy" refers to $C_1$-$C_5$-alkyl groups having an alkoxy substituent, including 2-ethoxyethyl and the like.

"Alkoxycarbonyl" refers to the group —C(O)OR where R includes H, "$C_1$-$C_6$-alkyl" or "aryl" or "heteroaryl" or "$C_1$-$C_6$-alkyl aryl" or "$C_1$-$C_6$-alkyl heteroaryl".

"$C_1$-$C_6$-alkyl alkoxycarbonyl" refers to $C_1$-$C_6$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl hetero-aryl".

"$C_1$-$C_6$-alkyl aminocarbonyl" refers to $C_1$-$C_6$-alkyl groups having an aminocarbonyl substituent, including 2-(dimethylaminocarbonyl)ethyl and the like.

"Acylamino" refers to the group —NRC(O)R' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl".

"$C_1$-$C_6$-alkyl acylamino" refers to $C_1$-$C_6$-alkyl groups having an acylamino substituent, including 2-(propionylamino)ethyl and the like.

"Ureido" refers to the group —NRC(O)NR'R" where each R, R', R" is independently hydrogen or "$C_1$-$C_6$-alkyl" or "aryl" or "heteroaryl" or "$C_1$-$C_6$-alkyl aryl" or "$C_1$-$C_6$-alkyl heteroaryl" "cycloalkyl" or "heterocycloalkyl", and where R' and R", together with the nitrogen atom to which they are attached, can optionally form a 3-8-membered heterocycloalkyl ring.

"$C_1$-$C_6$-alkyl ureido" refers to $C_1$-$C_5$-alkyl groups having an ureido substituent, including 2-(N'-methylureido)ethyl and the like.

"Amino" refers to the group —NRR' where each R,R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"$C_1$-$C_6$-alkyl amino" refers to $C_1$-$C_5$-alkyl groups having an amino substituent, including 2-(1-pyrrolidinyl)ethyl and the like.

"Ammonium" refers to a positively charged group —$N^+$RR'R", where each R,R',R" is independently "$C_1$-$C_6$-alkyl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Halogen" refers to fluoro, chloro, bromo and iodo atoms.

"Sulfonyloxy" refers to a group —$OSO_2$—R wherein R is selected from H, "$C_1$-$C_6$-alkyl", "$C_1$-$C_6$-alkyl" substituted with halogens, e.g., an —$OSO_2$—$CF_3$ group, "aryl", "heteroaryl", "$C_1$-$C_6$-alkyl aryl" or "$C_1$-$C_6$-alkyl heteroaryl".

"$C_1$-$C_6$-alkyl sulfonyloxy" refers to $C_1$-$C_6$-alkyl groups having a sulfonyloxy substituent, including 2-(methylsulfonyloxy)ethyl and the like.

"Sulfonyl" refers to group "—$SO_2$—R" wherein R is selected from H, "aryl", "heteroaryl", "$C_1$-$C_6$-alkyl", "$C_1$-$C_6$-alkyl" substituted with halogens, e.g., an —$SO_2$—$CF_3$ group, "$C_1$-$C_6$-alkyl aryl" or "$C_1$-$C_6$-alkyl heteroaryl".

"$C_1$-$C_6$-alkyl sulfonyl" refers to $C_1$-$C_6$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., an —SO—$CF_3$ group, "aryl", "heteroaryl", "$C_1$-$C_6$-alkyl aryl" or "$C_1$-$C_6$-alkyl heteroaryl".

"$C_1$-$C_6$-alkyl sulfinyl" refers to $C_1$-$C_6$-alkyl groups having a sulfinyl substituent, including 2-(methylsulfinyl)ethyl and the like.

"Sulfanyl" refers to groups —S—R where R includes "$C_1$-$C_6$-alkyl" or "aryl" or "hetero-aryl" or "$C_1$-$C_6$-alkyl aryl" or "$C_1$-$C_6$-alkyl heteroaryl". Preferred sulfanyl groups include methylsulfanyl, ethylsulfanyl, and the like.

"$C_1$-$C_6$-alkyl sulfanyl" refers to $C_1$-$C_6$-alkyl groups having a sulfanyl substituent, including 2-(ethylsulfanyl)ethyl and the like.

"Sulfonylamino" refers to a group —$NRSO_2$—R' where each R, R' is independently hydrogen or "$C_1$-$C_6$-alkyl" or "aryl" or "heteroaryl" or "$C_1$-$C_6$-alkyl aryl" or "$C_1C_6$-alkyl heteroaryl".

"$C_1$-$C_6$-alkyl sulfonylamino" refers to $C_1$-$C_6$-alkyl groups having a sulfonylamino substituent, including 2-(ethylsulfonylamino)ethyl and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "$C_1$-$C_6$-alkyl aryl", "$C_1$-$C_6$-alkyl heteroaryl", "$C_1$-$C_6$-alkyl cycloalkyl", "$C_1$-$C_6$-alkyl heterocycloalkyl", "amino", "ammonium", "acyl", "acyloxy", "acylamino", "aminocarbonyl", "alkoxycarbonyl", "ureido", "aryl", "heteroaryl", "sulfinyl", "sulfonyl", "alkoxy", "sulfanyl", "halogen", "carboxy", trihalomethyl, cyano, hydroxy, mercapto, nitro, and the like. Alternatively said substitution could also comprise situations where neighbouring substituents have undergone ring closure, notably when vicinal functional substituents are involved, thus forming, e.g., lactams, lactons, cyclic anhydrides, but also acetals, thioacetals, aminals formed by ring closure for instance in an effort to obtain a protective group.

"Pharmaceutically acceptable salts or complexes" refers to salts or complexes of the below-identified compounds of formulae (I) and (II) that retain the desired biological activity. Examples of such salts include, but are not restricted to acid addition salts formed with inorganic acids (e.g., hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art, which specifically include the quarternary ammonium salt of the formula —NR,R',R"$^+$Z$^-$, wherein R, R', R" is independently hydrogen, alkyl, or benzyl, $C_1$-$C_6$-alkyl, $C_2$-$C_6$-alkenyl, $C_2$-$C_6$-alkynyl, $C_1$-$C_6$-alkyl aryl, $C_1$-$C_6$-alkyl heteroaryl, cycloalkyl, heterocycloalkyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded.

Said formula also comprises its tautomers, its geometrical isomers, its optically active forms as enantiomers, diastereomers and its racemate forms, as well as pharmaceutically acceptable salts thereof. Preferred pharmaceutically acceptable salts of the formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

The compounds according to the present invention are those of formula I.

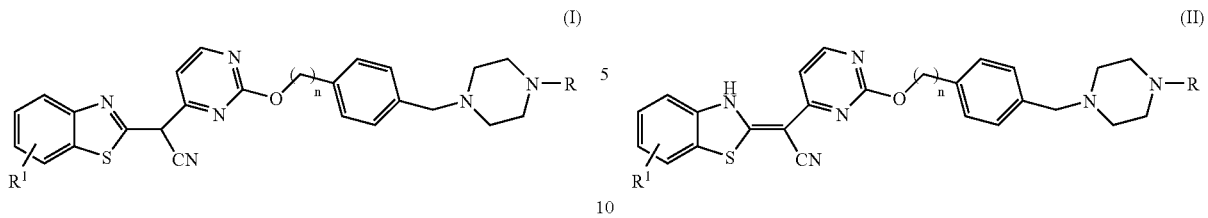

R in formula (I) is selected from the group comprising or consisting of hydrogen, substituted or unsubstituted $C_1$-$C_6$-alkyl, substituted or unsubstituted $C_1$-$C_6$-alkyl aryl, substituted or unsubstituted heteroaryl, substituted or unsubstituted $C_1$-$C_6$-alkyl heteroaryl, substituted or unsubstituted $C_2$-$C_6$-alkenyl, substituted or unsubstituted $C_2$-$C_6$-alkenyl aryl, substituted or unsubstituted $C_2$-$C_6$-alkenyl heteroaryl, substituted or unsubstituted $C_2$-$C_6$-alkynyl, substituted or unsubstituted $C_2$-$C_6$-alkynyl aryl, substituted or unsubstituted $C_2$-$C_6$-alkynyl heteroaryl, substituted or unsubstituted $C_3$-$C_8$-cycloalkyl, substituted or unsubstituted heterocycloalkyl, substituted or unsubstituted $C_1$-$C_6$-alkyl cycloalkyl, substituted or unsubstituted $C_1$-$C_6$-alkyl heterocycloalkyl, substituted or unsubstituted $C_1$-$C_6$-alkyl carboxy, acyl, substituted or unsubstituted $C_1$-$C_6$-alkyl acyl, acyloxy, substituted or unsubstituted $C_1$-$C_6$-alkyl acyloxy, substituted or unsubstituted $C_1$-$C_6$-alkyl alkoxy, alkoxycarbonyl, substituted or unsubstituted $C_1$-$C_6$-alkyl alkoxycarbonyl, aminocarbonyl, substituted or unsubstituted $C_1$-$C_6$-alkyl aminocarbonyl, acylamino, substituted or unsubstituted $C_1$-$C_6$-alkyl acylamino, ureido, substituted or unsubstituted $C_1$-$C_6$-alkyl ureido, amino, substituted or unsubstituted $C_1$-$C_6$-alkyl amino, sulfonyloxy, substituted or unsubstituted $C_1$-$C_6$-alkyl sulfonyloxy, sulfonyl, substituted or unsubstituted $C_1$-$C_6$-alkyl sulfonyl, sulfinyl, substituted or unsubstituted $C_1$-$C_6$-alkyl sulfinyl, sulfanyl, substituted or unsubstituted $C_1$-$C_6$-alkyl sulfanyl, sulfonylamino, substituted or unsubstituted $C_1$-$C_6$-alkyl sulfonylamino.

$R^1$ is selected from the group comprising or consisting of H, halogen, cyano, nitro, amino, substituted or unsubstituted $C_1$-$C_6$-alkyl, in particular $C_1$-$C_3$ alkyl, like methyl or ethyl or —$CF_3$, substituted or unsubstituted $C_2$-$C_6$-alkenyl, substituted or unsubstituted $C_2$-$C_6$-alkynyl, substituted or unsubstituted $C_1$-$C_6$-alkyl-aryl, substituted or unsubstituted aryl or substituted or unsubstituted heteroaryl, substituted or unsubstituted $C_1$-$C_6$-alkyl-heteroaryl, —C(O)—$OR^2$, —C(O)—$R^2$, —C(O)—$NR^2R^{2'}$, —$(SO_2)R^2$, with $R^2$ and $R^{2'}$ being independently selected from the group comprising or consisting of hydrogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted aryl, unsubstituted or substituted heteroaryl, unsubstituted or substituted $C_1$-$C_6$-alkyl aryl, unsubstituted or substituted $C_1$-$C_6$-alkyl heteroaryl. Preferably $R^1$ is H.

n is an integer from 0 to 3, more preferred is 1.

According to a more preferred embodiment piperazine benzothiazole derivative according to the present invention are those wherein R is hydrogen, $C_1$-$C_3$ alkyl, aminocarbonyl, $C_1$-$C_6$-alkyl alkoxycarbonyl, $C_1$-$C_6$-alkyl alkoxy, $C_1$-$C_6$-alkyl acyloxy, alkoxycarbonyl, $C_1$-$C_6$-alkyl aminocarbonyl. Specifically, R H, or $C_1$-$C_3$ alkyl, in particular a methyl or an ethyl moiety, or $C_1$-$C_6$-alkyl alkoxy.

The present invention also comprises the corresponding tautomers having the following formula:

Specific piperazine benzothiazole derivatives according to the present invention are selected from the following group:

1,3-benzothiazol-2-yl[2-({4-[(4-methylpiperazin-1-yl)methyl]benzyl}oxy)pyrimidin-4-yl]acetonitrile 1,3-benzothiazol-2-yl[2-({4-[(4-benzyl-piperazin-1-yl)methyl]-benzyl}oxy)pyrimidin-4-yl]acetonitrile 1,3-benzothiazol-2-yl(2-{[4-(piperazin-1-ylmethyl)benzyl]oxy}pyrimidin-4yl)acetonitrile 1,3-benzothiazol-2-yl[2-({4-[(4-formylpiperazin-1-yl)methyl]benzyl}oxy)pyrimidin-4-yl]acetonitrile

[2-({4-[(4-acetylpiperazin-1-yl)methyl]benzyl}oxy)pyrimidin-4-yl](1,3-benzothiazol-2-yl)acetonitrile (3H-Benzothiazol-2-ylidene)-{2-[4-(4-[1,2,4]oxadiazol-3-ylmethyl-piperazin-1-ylmethy)-benzyloxy]-pyrinmidin-4-yl}-acetonitrile 4-(4-{4-[(3H-Benzothiazol-2-ylidene)-cyano-methyl]-pyrimidin-2-yloxymethyl}-benzyl) -piperazine-1-carboxylic acid methyl ester 2-[4-(4-{4-[(3H-Benzotiazol-2-ylidene)-cyano-methyl]-pyrimidin-2-yloxymethyl}-benzyl)-piperazin-1-yl]-acetamide (2-{4-[4-(2-Amino-acetyl)-piperazin-1-ylmethyl]-benzyloxy}-pyrimidin-4yl)-(3H-benzothiazol-2-ylidene)-acetonitrile

[4-(4-{4-[(3H-Benzothiazol-2-ylidene)-cyano-methyl]-pyrimidin-2-yloxymethyl}-benzyl)-piperazin-1-yl]-acetic acid methyl ester (3H-Benzothiazol-2-ylidene)-(2-{4-[4-(2-methoxy-ethyl)-piperazin-1-ylmethyl]-benzyloxy}-pyrimidin-4yl)-acetonitrile 4-(4-{4-[(3H-Benzothiazol-2-ylidene)-cyano-methyl]-pyrimidin-2-yloxymethyl}-benzyl)-piperazine-1-carboxylic acid dimethylamide (3H-Benzothiazol-2-ylidene)-{2-[4-(4-ethyl-piperazin-1-ylmethyl)-benzyloxy]-pyrimidin-4-yl}-acetonitrile (3H-Benzothiazol-2-yliden)-(2-{4-[4-(2-hydroxy-ethyl)-piperazin-1-ylmethyl]-benzyloxy}-pyrimidin-4-yl)-acetonitrile The present invention also includes the geometrical isomers, the optical active forms, enantiomers, diastereomers of compounds according to formula I, as well as their racemates and also pharmaceutically acceptable salts, as well as the pharmaceutically active piperazine benzothiazole derivatives of formula I.

The compounds of the present invention are inhibitors of JNKs, in particular of JNK3 and may therefore be used in the treatment of disorders mediated by JNKs. Surprisingly, the compounds of the present invention show a considerable capacity to cross the blood-brain barrier (BBB) and are therefore particularly useful in the treatment of cerebral ischemic disorders or CNS disorders. Hence, a further aspect of the present invention consists in the use of the piperazine benzothiazole derivatives of the present invention in the treatment and/or prophylaxis of cerebral ischemic disorders or CNS disorders.

A further aspect of the present invention is related to the use of the piperazine benzothiazole derivatives according to formula I or II for the preparation of pharmaceutical compositions for the treatment of cerebral ischemic disorders or CNS disorders.

Still a further object of the present invention is a process for preparing the novel benzo-thiazole derivatives according to formulae I or II. A general synthetic access to the compounds according to formula I is set out in scheme I.

Scheme I

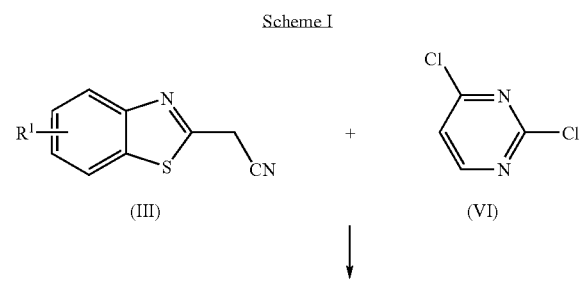

As illustrated in the above scheme I, the starting compounds of formula III are reacted with (suitably substituted (activated) pyrimidines), like halogeno pyrimidines, e.g. 2,4-dichloro-pyrimidine of formula VI to provide the pyrimidino-benzothiazole compounds IV. Preferably such reactions are performed in the presence of suitable bases, e.g. sodium hydride, potassium hydride and the like in an anhydrous inert atmosphere, preferably in a polar solvent like DMF, DMA, MeCN or THF at a temperature in the range of about −78° C. to 100° C.

Benzothiazbles of formula m are either commercially available, such as from Maybridge Chemical Co. Ltd or can be prepared from commercially available compounds by conventional procedures.

Halogenated pyrimidines, e.g. 2,4-dichloropyrimidine of formula VI, are also either commercially available, such as from Aldrich, Fluka, Sigma and the like or may be prepared by conventional procedures.

For obtaining the final piperazine benzothiazoles of formula (I), the intermediate compounds of formula (IV) are preferably reacted with suitable alcohols of formula (V), as illustrated in scheme II.

Scheme II

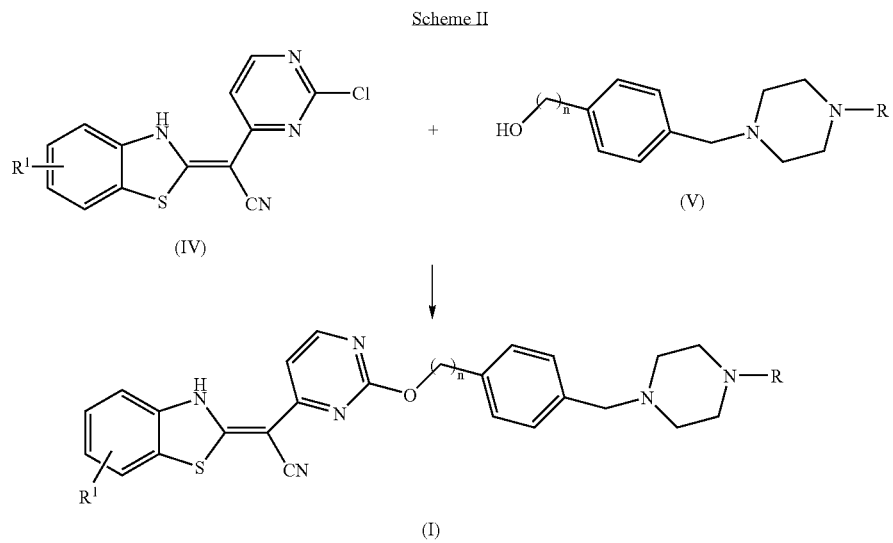

-continued

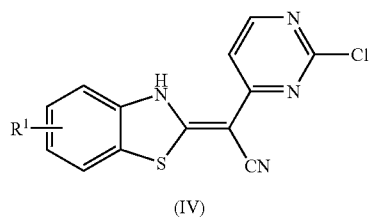

The reaction is preferably performed in the presence of solvents such as DMF, DMA, NMP, DMSO, OR CAN, most preferably in DMA or MeCN, in the presence of a suitable base such as tBuOK, $Cs_2CO_3$, (Cesium carbonate), with or without CuI, NaH, or the like, most preferably NaH, at a temperature in the range of about 25 to 120° C. In a preferred method, the starting compounds are heated to 25° up to 100° C. in solution in DMA in the presence of NaH.

The intermediate compounds of formula (V) may be obtained by a synthetic approach which is illustrated in scheme III. In said scheme III the staring building block is methyl-p-toluate to prepare a benzyl alcohol. In the case of a phenethylalcohol or a phenylpropyl alcohol according to formula (V), methyl-p-toluate may be replaced by the appropriate starting materials, commercially available or prepared by conventional methods.

Scheme III

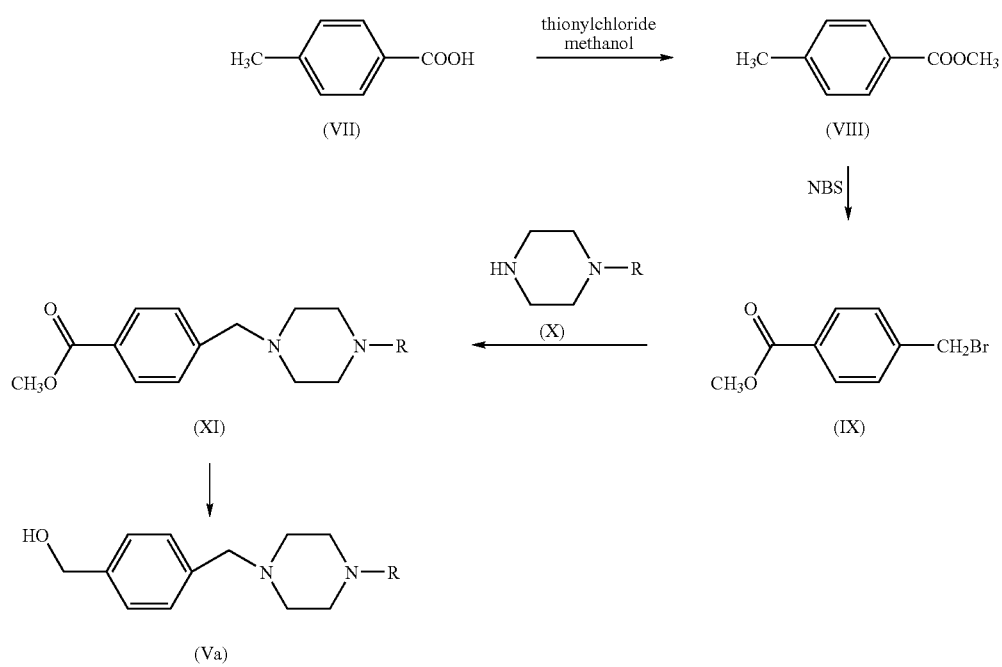

As used herein, "treating" refers to inhibiting or arresting the development of a disease, disorder or condition and/or causing the reduction, remission or regression of the symptoms of a disease, disorder or condition. Those of skill in the art will understand that various methodologies and assays may be used to assess the development of a disease, disorder or condition, and similarly, various methodologies and assays may be used to assess the reduction, remission or regression of the symptoms of a disease, disorder or condition.

When employed as pharmaceuticals, the piperazine benzothiazole derivatives of the present invention are typically administered in the form of a pharmaceutical composition. Hence, pharmaceutical compositions comprising a compound of formula I and a pharmaceutically acceptable carrier, diluent or excipient therefore are also within the scope of the present invention. A person skilled in the art is aware of a whole variety of such carrier, diluent or excipient compounds suitable to formulate a pharmaceutical composition. Also, the present invention provides compounds for use as a medicament.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

The pharmaceutical compositions of these inventions can be administered by a variety of routes including oral, rectal, transdermal, subcutaneous, intravenous, intramuscular; intrathecal, intraperitoneal and intranasal. Depending on the intended route of delivery, the compounds are preferably formulated as either injectable, topical or oral compositions.

The compositions for oral administration may take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient Typical unit dosage forms include prefilled, premeasured ampoules or syringes of the liquid compositions or pills, tablets, capsules or the like in the case of solid compositions. In such compositions, the piperazine benzothiazole compound is usually a minor component (from about 0.1 to about 50% by weight or preferably from about 1 to about 40% by weight) with the remainder being various vehicles or carriers and processing aids helpful for forning the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the piperazine benzothiazole derivatives of formula I in such compositions-is typically a minor component, frequently ranging between 0.05 to 10% by weight with the remainder being the injectable carrier and the like.

The above-described components for orally administered or injectable compositions are merely representative. Further materials as well as processing techniques and-the like are set out in Part 8 of *Remington's Pharmaceutical Sci-* ences, 17th Edition, 1985, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences.*

In the following the present invention shall be illustrated by means of some examples which are not construed to be viewed as limiting the scope of the invention.

In the following the present invention shall be illustrated by means of some examples which are not construed to be viewed as limiting the scope of the invention.

The HPLC, NMR and MS data provided in the examples described below were obtained as followed: HPLC: column Waters Symmetry C8 50×4.6 mm, Conditions: a—MeCN/$H_2O$ 0.09% TFA, 0 to 100% (10 min); b—MeCN/$H_2O$, 5 to 100% (8 min), max plot 230-400 nm; Mass spectra: PE-SCIEX API 150 EX (APCI and ESI), LC/MS spectra: Waters ZMD (ES); $^1$H-NMR: Bruker DPX-300 MHz.

The purifications were obtained as followed: Preparative HPLC Waters Prep LC 4000 System equipped with columns Prep Nova-Pak®HR C186 µm 60 Å, 40×30 mm (up to 100 mg) or 40×300 mm (up to 1 g). All the purifications were performed with a gradient of MeCN/$H_2O$ 0.09% TFA.

EXAMPLE A

Preparation of the Intermediate Compound (IV); (see Scheme 1) 1,3-benzothiazol-2-yl(2-chloro-4-pyrimidinyl)-acetonitrile To a stirred suspension of NaH (60% in oil, 9.2 g, 0.23 mol) in dry THF (200 ml) was added drop wise under inert atmosphere a solution of 1,3-benzothiazol-2yl-acetonitrile (20 g, 0.15 mol) in dry THF (200 ml). After 1 h30 stirring at r.t., a solution of 2,4-dichloropyri-midine (17.1 g, 0.15 mol) in dry THF (200 ml) was added dropwise. The reaction mixture was allowed to stir under inert atmosphere at r.t. until complete disappearance of the starting material. The reaction was quenched by addition of water and the THF was evaporated. Water was added and the suspension was slightly acidified with aqueous HCl 1M. The precipitate obtained was filtered off and washed thoroughly with water until neutral then with hexane to remove the oil. The crude solid was dried under vacuum at 40° C., affording 28 g (84%) of the title compound as a light brown powder: mp 246° C. dec.; MS: 286.8 (M+1); HPLC (Conditions a, 268 nm) 97%, rt.5.66 min; $^1$HNMR (DMSO-d6) δ 13.25 (br s, 1H, exchangeable), 8.09 (d, J=4.14 Hz, 1H), 7.90 (d, J=7.53 Hz, 1H), 7.61 (d, J=7.92 Hz, 1H), 7.39-7.34 (m, 1H), 7.20-7.15 (m, 1H), 6.96 (br d, 1H). CHN analysis: $C_{13}H_7ClN_4S$: Calculated: C, 54.19%, H 2.48%; N 19.45%; Found: C 53.35%, H 2.77%, N 17.62%.

EXAMPLE B

Preparation of the Intermediate Compound (Va), (see Scheme 3) (4-(4-methyl-piperazin-1-ylmethyl-phenyl)-methanol Step 1: Methyl-p-toluate To a solution of p-toluic acid (175 g, 1.28 mol) in methanol (2 L) was added dropwise thionylchloride (612 g, 5.14 mol) under stiring at 5° C. The mixture was refluxed overnight, then the solvent evaporated. The residue obtained was treated with a 10% aqueous $NaHCO_3$ solution (pH~8) The product was extracted with ethyl acetate, washed-with water and dried. The solvent was removed and the crude was purified by column chromatography (pet ether/ethyl acetate) to give methyl-p-toluate as colorless liquid (180 g, 93%).

Step 2: 4-Methoxy carbonyl benzyl bromide

To a mixture of methyl-p-toluate (180 g, 1.2 mol) and N-bromosuccimide (235 g, 1.32 mol) in $CCl_4$ (2 L) was added in portion benzoyl peroxide (18 g, 0.1 times) at 50° C. The mixture was refluxed for 5 h. Then the mixture was allowed to cool down to 40° C. and the solid was filtered off. The filtrate was concentrated to give 4-methoxy carbonyl benzyl bromide (252 g, 91%) as light yellow liquid.

Step 3: N-methyl(4-Methoxycarbonylbenzyl)piperazine

To a solution of N-methyl piperazine (80 g, 0.91 mol) and triethylamine (232 g, 2.29 mol) in absolute alcohol (1750 ml) was added dropwise at 0° C. a solution of 4-methoxycarbonyl-benzyl bromide (252 g, 1.1034 mol) in absolute alcohol (250 ml). The mixture was stirred overnight at RT. Then the mixture was concentrated and the residue obtained was taken up in 1.5N HCl (3 L) then washed with diethyl ether (3 times) and ethyl acetate. The solution was neutralized with a 10% aqueous NaOH solution and basified up to pH=8 with a 10% aqueous $NaHCO_3$ solution. The product was extracted with $CHCl_3$, washed with water and brine then dried over $Na_2SO_4$. The solvent was removed and the crude was purified by column chromatography $CHCl_3$/MeOH to give N-methyl(4-methoxy carbonyl benzyl)piperazine (150 g, 70%) as a brown liquid.

Step 4: (4-(4-Methyl-piperazin-1-ylmethyl-phenyl)-methanol

To a mixture of LAH (36 g, 0.957 mol) in dry THF (1750 ml) was added dropwise at 0° C. under $N_2$ a solution of N-(4-methoxycarbonyl benzyl) bromide (150 g, 0.638 mol) in dry THF (250 ml). The mixture was stirred overnight at RT under $N_2$, then quenched with a 10% aqueous NaOH solution. The solid was filtered off and the filtrate was concentrated. The residue was taken up in DCM (1 L) and washed with water. The solvent evaporated to give N-methyl (4-hydroxymethylbenzyl)piperazine (96 g, 73%) as light yellow liquid.

M$^+$(ES):221.2

$^1$H NMR (DMSO-d6) δ 7.26-7.19 (m, 4H), 5.11 (t, J=5.65 Hz, 1H), 4.45 (d, j=5.65 Hz, 2H), 3.40 (s, 2H), 3.39-2.20 (m, 8H), 2.12 (s, 3H)

In a similar way the following intermediate compounds may be obtained.

(3-(4-Methyl-piperazin-1-ylmethyl-phenyl)-methanol $^1$H NMR (DMSO-d6) δ 7.27-7.11 (m, 4H), 5.17-5.13 (m, 1H), 4.48-4.46 (m, 2H), 3.41 (s, 2H), 2.41-2.21 (m, 8H), 2.13 (s, 3H)

4-(4-Hydroxymethyl-benzyl)-piperazin-1-carboxylic acid tert-butyl ester

M$^+$(ES): 307.2

$^1$H NMR (DMSO-d6) δ 7.27-7.21 (m, 4H), 5.12 (t, J=5.65 Hz, 1H), 4.46 (d, J=5.65 Hz, 2H), 3.43 (s, 2H), 3.28 (br t, 4H), 2.27 (t, J=4.9 Hz, 4H), 1.40 (s, 9H).

{4-[(4-ethylpiperazin-1-yl)methyl]phenyl}methanol

Y=78%, M$^+$(ES): 235.3;

$^1$H NMR (DMSO-d6) δ 7.26-7.19 (m, 4H), 5.12 (t, J=5.6 Hz, 1H), 4.46 (br d, 2H), 3.33 (s, 2H), 2.44-2.20 (m, 8H), 2.27 (q, J=7.2 Hz, 2H), 0.95 (t, J=7.2 Hz, 3H).

(4-{[4-(2-methoxyethyl)piperazin-1-yl]methyl}phenyl) methanol

Y=66%, M$^+$(ES): 265;

$^1$H NMR (DMSO-d6) δ 7.23-7.22 (m, 4H), 5.11 (t, J=5.7 Hz, 1H), 4.45 (br d, 2H), 3.40 (s, 2H), 3.38 (t, J=5.9 Hz, 2H), 3.20 (s, 3H), 2.42 (t, J=5.9 Hz, 2H), 2.48-2.25 (m, 8H).

(4-{[4-benzyl-piperazin-1-yl]methyl}phenyl)methanol; Y=78%, M+(ES): 297

EXAMPLE 1

Preparation of 1,3-benzothiazol-2-yl[2-({4-[(4-methylpiperazin-1-yl)methyl]-benzyl}-oxy)pyrimidin-4yl]acetonitrile (trimesylate salt) (see Scheme 2)

To a suspension of NaH (60% in oil, 1.68 g, 69.75 mmol) in dry DMA (80 ml) was added a solution of (4-(4-methyl-piperazin-1-ylmethyl-phenyl)-methanol (compound of formula V in scheme 2) (7.68 g, 34.88 mmol) in dry DMA (80 ml). The resulting suspension was stirred 1 h at r.t. under inert atmosphere. A solution of IV (5 g, 17.44 mmol) in DMA (80 ml) was added drop wise and the suspension was stirred at 100° C. under inert atmosphere. After 4 hours the reaction was cooled down and quenched by addition of water. The solvents were evaporated and the residue was taken up in water (100 ml). 10 mL of EtOAc and cyclohexane were added to trap the residual oil from NaH and the solution was stored at 4° C. for a day. The precipitate formed was filtered off and washed with water until neutral pH then with cyclohexane, affording 6.17 g of crude base.

3.5 g of the crude base was taken up in water (125 ml) and 1.25 ml of methane sulfonic acid was added. The solution was lyophilised to give an orange-yellow solid which was washed with ACN and dried under vacuum at 30° C. to afford 4.99 g (Yield=66%) of the title compound as a yellow powder.

$M^{31}$ (ESI): 469.1; $M^+$(ESI): 471.16; HPLC (Conditions b, max plot) %, rt. 2.01 min.

$^1$H NMR (DMSO-d6) δ 10.30 (very br s, 1H), 8.06-8.03 (m, 2H), 7.82 (d, J=8.3 Hz, 1H), 7.76 (d, J=7.9 Hz, 2H), 7.69 (d, J=7.9 Hz, 2H), 7.56-7.51 (m, 1H), 7.40-7.35 (m, 1H), 6.88 (br d, 1H), 5.82 (s, 2H), 4.52 (s, 2H), 3.85-3.57 (m, 4H), 3.48-3.26 (m, 4H), 2.95 (s, 3H), 2.48 (s, 9H).

EXAMPLE 2

Preparation of 1,3-benzothiazol-2-yl[2-({4-[(4-benzyl-piperazin-1-yl)methyl]-benzyl}oxy)pyrimidin-4-yl]acetonitrile (2Mes)

The title compound was obtained by performing the same protocol set out in the above example 1, whereby (4-(4-benzyl-piperazin-1-ylmethyl-phenyl)-methanol is used instead of (4-(4-methyl-piperazin-1-ylmethyl-phenyl)-methanol.

Y: 42%; $M^-$(ESI) 545.7; $M^+$(ESI) 547.2; HPLC (Conditions b, max plot) 99.8%, rt. 2.52 min.

$^1$H NMR (DMSO-d6) δ 7.95-7.93 (m, 2H), 7.73 (d, J=7.9 Hz, 1H), 7.67-7.64 (m, 2H), 7.56-7.40 (m, 8H), 7.29-7.24 (m, 1H), 6.75 (br d, 1H), 5.73 (s, 2H), 4.45-4.15 (m, 4H), 3.60-3.30 (m, 4H), 3.25, 2.90 (m, 4H).

EXAMPLE 3

Preparation of (3H-Benzothiazol-2-ylidene)-{2-[4-(4-ethyl-piperazin-1-ylmethyl)-benzyloxy]-pyrimidin-4-yl}-acetonitrile The title compound was obtained by performing the same protocole set out in the above example 1, whereby {4-[(4-ethylpiperazin-1-yl)methyl]phenyl}methanol is used instead of (4-(4-methyl-piperazin-1-ylmethyl-phenyl)-methanol.

Y=: 83%, $M^+$(ES): 485.18; HPLC (Conditions b, max plot) 97.8%, rt. 2.06 min.

$^1$H NMR (DMSO-d6) δ 7.95 (d, J=7.9 Hz, 1H), 7.90 (br d, 1H), 7.74 (d, J=7.9 Hz, 1H), 7.67 (d, J=7.9 Hz, 2H), 7.58 (d, J=7.9 Hz, 1H), 7.45-7.40 (m, 1H), 7.30-7.24 (m, 1H), 6.73 (br d, 1H), 5.73 (s, 2H), 4.32 (s, 2H), 4.42-4.23 (m, 2H), 3.76-3.38 (m, 4H), 3.32-2.89 (m, 4H), 1.21 (t, J=7.1 Hz, 3H)

EXAMPLE 4

Preparation of (3H-Benzothiazol-2-ylidene)-(2-{4-[4-(2-methoxy-ethyl)-piperazin-1-ylmethyl]-benzyloxy}-pyrimidin-4-yl)-acetonitrile (3TFA)

The title compound was obtained by performing the same protocole set out in the above example 1 whereby (4-{[4-(2-methoxyethyl)piperazin-1-yl]methyl}phenyl)methanol is used instead of (4-(4-methyl-piperazin-1-ylmethyl-phenyl)-methanol.

Y=: 33%, $M^+$(ES): 515.06; HPLC (Conditions b, max plot) 99.5%, rt. 2.10 min.

$^1$H NMR (DMSO-d6) δ 7.93 (d, J=7.9 Hz, 1H), 7.87 (br d, 1H), 7.74 (d, J=8.3 Hz, 1H), 7.63 (d, J=7.9 Hz, 2H), 7.50 (d, J=7.9 Hz, 2H), 7.44-7.39 (m, 1H), 7.28-7.23 (m, 1H), 6.70 (br d, 1H), 5.71 (s, 2H), 4.10 (s, 2H), 3.63-3.60 (m, 2H) 3.50-2.90 (m, 13H).

EXAMPLE 5

Preparation of 1,3-benzothiazol-2-yl(2-{[4-piperazin-1-ylmethyl)benzyl]oxy}-pyrimidin-4-yl)acetonitrile (3TFA)

The title compound was obtained by performing the same protocole set out in the above example 1, whereby 4-(4-Boc-piperazin-1-ylmethyl-phenyl)-methanol is used instead of (4-(4-methyl-piperazin-1-ylmethyl-phenyl)-methanol. Thus, a Boc protected crude base is obtained.

The Boc protected crude base was taken up in a mixture of DCM/TFA (9:1) and stirred 2 hours at r.t. The DCM was evaporated at r.t. The residue was triturated in ether then filtered off and dried under vacuum at r.t. ON (over night). After purification by preparative HPLC, the pure fractions were gathered and lyophilised affording 3.03 g (34%) of the title compound as a yellow powder.

Y=34%; $M^-$(ES) 455.2; $M^+$(ES) 457.4; HPLC (Conditions b, max plot) 99.7%, rt. 1.98 min;

$^1$H NMR (DMSO-d6) δ 9.00 (br s, 1H), 7.93 (d, J=7.6 Hz, 1H), 7.87 (br d, 1H), 7.74 (d, J=7.9 Hz, 1H), 7.63 (d, J=7.9 Hz, 2H), 7.51 (d, J=7.9 Hz, 2H), 7.45-7.39 (m, 1H), 7.28-7.23 (m, 1H), 6.72 (d, J=6.4 Hz, 1H), 5.71 (s, 2H), 4.10 (s, 2H), 3.32-3.18 (m, 4H), 3.13-2.92 (m, 4H)

EXAMPLE 6

Preparation of 1,3-benzothiazol-2-yl[2-({4-[(4-formylpiperazin-1-yl)methyl]-benzyl}oxy)pyrimidin-4-yl]acetomitrile (2TFA)

The Boc-deprotected crude base obtained in example 3 (0.6 g, 1.31 mmol) was suspended in 15 ml of methylformate in a sealed vessel. The reaction mixture was stirred at 40° C. for 15 days then cooled down to r.t. The precipitate formed was filtered off then washed with water and the crude product was purified by preparative HPLC. The pure fractions were gathered and lyophilised affording 0.26 g of the title compound as a yellow powder.

Y=28%; $M^-$(ES) 483.3; $M^+$(ES) 485.5; HPLC (Conditions b, max plot) 99.7%, rt. 2.18 min.

$^1$H NMR (DMSO-d6) d 9.95 (br s, 1H), 8.03 (s, 1H), 7.93 (d, J=7.9 Hz, 1), 7.96-7.84 (very br d, 1H), 7.73 (d, J=7.9 Hz, 1H), 7.68 (d, J=7.9 Hz, 2H), 7.54 (d, J=7.9 Hz, 2H), 7.47-7.40 (m, 1H), 7.29-7.24 (m, 1H), 6.73 (br d, 1H), 5.73 (s, 2H), 4.36 (s, 2H), 4.05-2.80 (m, 8H)

EXAMPLE 7

Preparation of (2-{4-[4-(2-Amino-acetyl)-pinerazin-1-ylmethyl]-benzyloxy}-pyrimidin-4-yl)-(3H-benzothiazol-2-ylidene)-acetonitrile (2Mes) (3TFA, To a DMA solution (40 ml) of Boc-deprotected crude product (2.9 g, 3.65 mmol) obtained in example 5 was added amberlyst A21 (0.7 g, 3.76 mmol) and the solution was stirred at r.t. for 20 min. The resin was filtered off and to the filtrate were added a solution of Boc Glycine (0.74 g, 4 mmol), HOBt (0.73 g, 5.47 mmol), EDC (1.05 g, 5.47 mmol) and DIPEA (1.9 g, 14.6 mmol) in DMA (30 ml). The resulting solution was stirred overnight at r.t. After evaporation of the solvent under reduced pressure, the residue obtained was suspended in a mixture of MeOH and EtOAc and left overnight at 4° C. The precipitate was filtered off, washed with EtOAc and dried under vacuum at 40° C., affording 1.04 g of the title compound as a yellow solid.

Y=10%, M⁺(ES): 514.06; HPLC (Conditions b, max plot) 99.9%, rt. 2.00 min.

¹H NMR (DMSO-d6) δ 8.13-8.02 (m, 2H), 7.94-7.91 (m, 2H), 7.73 (br d, 1H), 7.67 (d, J=7.9 Hz, 2H), 7.54 (d, J=7.9 Hz, 2H), 7.45-7.40 (m, 1H), 7.29-7.24 (m, 1H), 6.74 (br d, 1H), 5.74 (s, 2H), 4.34 (s, 2H), 3.89 (s, 2H), 3.73-3.10 (m, 8H)

EXAMPLE 8

Preparation of [2-({4-[(4-acetylpiperazin-1-yl)methyl]benzl}oxy)pyrimidin-4-yl](1,3-benzothiazol-2-yl)acetonitrile (2TFA)

To a DMA solution (6 ml) of Boc-deprotected crude product (0.3 g, 0.66 mmol) obtained in example 5 were added triethylamine (0.09 ml, 0.66 mmol) and acetyl chloride (0.09 ml, 1.31 mmol) and the solution was stirred 5 min at r.t. The reaction mixture was concentrated to near dryness and the residue obtained was purified by preparative, HPLC. The pure fractions were gathered and lyophilised affording 0.1 g (21%) of the title compound as a yellow powder.

M⁻(ES) 496.9; M⁺(ES) 499.1; HPLC (Conditions b, max plot) 99%, rt. 2.19 min.

¹H NMR (DMSO-d6) δ 10.05 (br s, 1H), 7.93 (d, J=7.9 Hz, 1H), 7.93-7.84 (very br d, 1H), 7.74 (d, J=7.9 Hz, 1H), 7.67 (d, J=8 Hz, 2H), 7.54 (d, J=7.9 Hz, 2H), 7.45-7.39 (m, 1H), 7.29-7.24 (m, 1H), 6.72 (br d, 1H), 5.73 (s, 2H), 4.36 (s, 2H), 4.02-3.87 (m, 1H), 3.42-2.75 (m, 7H), 2.01 (s, 3H).

EXAMPLE 9

Preparation of 4-(4-{4-[(3H-Benzothiazol-2-ylidene)-cyano-methyl]-pyrimidin-2-yloxymethyl}-benzyl)-piperazine-1-carboxylic acid dimethylamide (2TFA)

To a DMA solution (12 ml) of Boc-deprotected crude product (0.5 g, 0.63 mmol) obtained in example 5 were added amberlyst A21 (1.12 g, 5.35 mmol) and dimethylcarbamoyl chloride (0.12 ml, 1.31 mmol) and the solution was stirred at 0° C. for 1 h. As no product was formed, the solution was warmed up to r.t. for 12 days to obtain a complete disappearance of the starting material. Amberlyst was filtered off and water was added to the filtrate. As no precipitate was formed, the solvents were evaporated under reduced pressure and the residue was taken up in water and lyophilised. The residue obtained was purified by preparative HPLC. The pure fractions were gathered and lyophilised affording 85 mg of the title compound as a yellow solid.

Y=18%, M⁺(ES): 528.09; HPLC (Conditions b, max plot) 98.9%, rt. 2.32 min.

¹H NMR (DMSO-d6) δ 9.82 (very br s, 1H), 7.94-7.86 (m, 2H), 7.73 (d, J=7.9 Hz, 1H), 7.67 (d, J=7.9 Hz, 2H), 7.55 (d, J=7.9 Hz, 2H), 7.44-7.39 (m, 1H), 7.28-7.23 (m, 1H), 6.72 (br d, 1H), 5.73 (s, 2H), 4.37 (s, 2H), 3.65-3.48 (m, 2H), 3.32-3.18 (m, 2H), 3.11-2.90 (m, 4H), 2.74 (s, 6H)

In a similar way the following compound may be obtained.

4-(4-{4-[(3H-Benzothiazol-2-ylidene)-cyano-methyl]-pyrimidin-2-yloxymethyl}-benzyl)-piperazine-1carboxylic acid methyl ester (2TFA)

Y=32%, M⁺(ES): 514.85; HPLC (Conditions b, max plot) 99%, rt. 2.36 min.

¹H NMR (DMSO-d6) δ 7.94-7.91 (m, 2H), 7.73 (br d, 1H), 7.66 (d, J=7.9 Hz, 7.9 Hz, 2H), 7.53 (d, J=7.9 Hz, 2H), 7.46-7.40 (m, 1H), 7.29-7.24 (m, 2H), 6.73 (br d, 1H), 5.73 (s, 2H), 4.34 (s, 2H), 4.13-3.92 (m, 2H), 3.63 (s, 3H), 3.60-2.94 (m, 6H)

EXAMPLE 10

Preparation of (3H-Benzothiazol-2-ylidene)-{2-[4-(4-[1,2,4]oxadiazol-3-ylmethyl-piperazin-1-ylmethyl)-berzyloxy]-pyrimidin-4-yl}-acetonitrile (3TFA)

To a DMA solution (10 ml) of Boc-deprotected crude product (0.5 g, 0.63 mmol) obtained in example 5 was added amberlyst A21 (0.7 g, 3.76 mmol) and the solution was stirred at r.t. for 20 min. The resin was filtered off and to the filtrate were added 3-(chloromethyl)-1,2,4-oxadiazole and potassium carbonate. The resulting suspension was stirred at r.t. for 48 h. Complete disappearance of the starting material was achieved after 3 days stirring at r.t and the addition of 2.4 Eq of 3-(chloromethyl)-1,2,4-oxadiazole. After filtration and removal of the solvent under reduced pressure, the residue obtained was purified by preparative HPLC. The pure fractions were gathered and lyophilised affording 110 mg of the title compound as a yellow solid.

Y=20%, M⁺(ES): 538.94; HPLC (Conditions b, max plot) 97%, rt. 2.31 min.

¹H NMR (DMSO-d6) δ 9.62 (s, 1H), 7.93-7.91 (m, 2H), 7.73 (d, J=7.9 Hz, 1H), 7.65 (d, J=7.9 Hz, 2H), 7.53 (d, J=7.9 Hz, 2H), 7.44-7.39 (m, 1H), 7.27-7.22 (m, 1H), 6.72 (br d, 1H), 5.72 (s, 2H), 4.32 (s, 2H), 3.85 (s, 2H), 3.34-3.17 (m, 2H), 3.12-2.88 (m, 4H), 2.58-2.41 (m, 2H)

In a similar way the following compounds may be obtained.

(3H-Benzothiazol-2-ylidene)-(2-{4-[4-(2-hydroxy-ethyl)-piperazin-1-ylmethyl]-benzyloxy}-pyrimidin-4-yl)-acetonitrile (3TFA)

Y=22%, M⁺(ES): 500.92; HPLC (Conditions b, max plot) 99.3%, rt. 2.03 min.

¹H NMR (DMSO-d6) δ 7.93 (d, J=7.9 Hz, 1H), 7.86 (very br d, 1H), 7.74 (br d, 1H), 7.58 (br d, 2H), 7.43-7.36 (m, 3H), 7.28-7.23 (m, 1H), 6.71 (br d, 1H), 5.69 (s, 2H), 4.20-3.60 (m, 4H), 3.70-3.67 (m, 2H), 3.52-3.34 (m, 2H), 3.20-2.92 (m, 4H)

[4-(4-{4-[(3H-Benzothiazol-2-ylidene)-cyano-methyl]-pyrimidin-2-yloxymethyl}-benzyl)-piperazin-1-yl]-acetic acid methyl ester (3TFA)

Y=14%, M⁺(ES): 528.85; HPLC (Conditions b, max plot) 98%, rt. 2.38 min.

¹H NMR (DMSO-d6) δ 7.94-7.91 (m, 2H), 7.73 (br d, 1H), 7.65 (d, J=7.9 Hz, 2H), 7.53 (d, J=7.9 Hz, 2H), 7.44-7.39 (m, 1H), 7.28-7.23 (m, 2H), 6.71 (br d, 1H), 5.72

(s, 2H), 4.30 (br s, 2H), 3.62 (s, 3H), 3.49-3.36 (m, 2H), 3.30-3.15 (m, 2H), 3.10-2.85 (m, 4H),2.73-2.54 (m, 2H)

2-[4-{4-[(3H-Benzothiazol-2-ylidene)-cyano-methyl]-pyrimidin-2-yloxymethyl}-benzyl)-piperazine-1-yl]-acetamide (3TFA)

Y=16%, M$^+$(ES): 513.95; HPLC (Conditions b, max plot) 93%, rt. 2.08 min.

$^1$H NMR (DMSO-d6) δ 7.93 (d, J=7.9 Hz, 1H), 7.88 (br d, 1H), 7.73 (d, J=7.9 Hz, 1H), 7.61 (d, J=7.9 Hz, 2H), 7.46 (br d, 2H), 7.45-7.40 (m, 1H), 7.28-7.23 (m, 1H), 6.72 (br d, 1H), 5.71 (s, 2H), 4.30-2.65 (m, 12H)

EXAMPLE 11

Preparation of a Pharmaceutical Formulation

The following formulation examples illustrate representative pharmaceutical compositions according to the present invention being not restricted thereto.

Formulation 1—Tablets

A piperazine benzothiazole compound of formula I is admixed as a dry powder with a dry gelatin binder in an approximate 1:2 weight ration. A minor amount of magnesium stearate is added as a lubricant The mixture is formed into 240-270 mg tablets (80-90 mg of active piperazine benzothiazole compound per tablet) in a tablet press.

Formulation 2—Capsules

A piperazine benzothiazole compound of formula I is admixed as a dry powder with a starch diluent in an approximate 1:1 weight ratio. The mixture is filled into 250 mg capsules (125 mg of active piperazine benzothiazole compound per capsule).

Formulation 3—Liquid

A piperazine benzothiazole compound of formula I (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A piperazine benzothiazole compound of formula I is admixed as a dry powder with a dry gelatin binder in an approximate 1:2 weight ratio. A minor amount of magnesium stearate is added as a lubricant The mixture is formed into 450-900 mg tablets (150-300 mg of active piperazine benzothiazole compound) in a tablet press.

Formulation 5—Injection

A piperazine benzothiazole compound of formula I is dissolved in a buffered sterile saline injectable aqueous medium to a concentration of approximately 5 mg/ml.

EXAMPLE 12

Biological Assays

The compounds of the present invention may be subjected to the following assays:

a) JNK2 and -3 in vitro assay:

The compounds of the present invention are inhibitors of JNKs, in particular of JNK2 and 3. The phosphorylation of c-jun by JNK2 or JNK3 may be determined by monitoring the incorporation of $^{33}$P into c-jun following the protocol below. The inhibitory activity of the compounds according to formula I, towards c-jun phosphorylation through JNK, is determined by calculating phosphorylation activity in the presence or absence of compounds according to formula I.

JNK3 and/or -2 assays are performed in 96 well MTT plates: incubation of 0.5 μg of recombinant, pre-activated GST-JNK3 or GST-JNK2 with 1 μg of recombinant, biotinylated GST-c-Jun and 2 μM $^{33}$γ-ATP (2 nCi/μl), in the presence or absence of compounds according to formula I and in a reaction volume of 50 μl containing 50 mM Tris-HCl, pH 8.0; 10 mM MgCl$_2$; 1 mM Dithiothreitol, and 100 μM NaVO$_4$. The incubation is performed for 120 min. at R.T. and stopped upon addition of 200 μl of a solution containing 250 μg of Streptavidine-coated SPA beads (Amersham, Inc.)*, 5 mM EDTA, 0.1% Triton X-100 and 50 μM ATP, in phosphate saline buffer.

After incubation for 60 minutes at RT, beads are sedimented by centrifugation at 1500×g for 5 minutes, resuspended in 200 μl of PBS containing 5 mM EDTA, 0.1% Triton X-100 and 50 μM ATP and the radioactivity measured in a scintillation β counter, following sedimentation of the beads as described above.

The tested compounds according to formula I display an inhibition (IC$_{50}$) with regard to JNK3 of less than 10 μM, preferably less than 1 μM and more preferred less than 0.25 μM.

b) Global Ischemia in Gerbils

The ability of the JNK inhibitors described in formula I to protect cell death during a stroke event may be assessed using the following protocol:

The gerbil bilateral carotid occlusion is a well-described animal model of acute ischemic stroke and involves relatively easy surgical techniques.

The neuronal degeneration in the hippocampus develops over several days and is often referred as "delayed neuronal death". In addition, the neurodegeneration observed histologically is obvious and easily quantified (11). Furthermore, the histopathology seen in the gerbil is similar to that observed in the hippocampal CA1 region of the human brain following a cardiac arrest. Behavior observations, such as memory tests, could even be performed in the case of gerbils. This kind of tests for appreciation of the degree of recovery is not easily manageable in other models such as in rat whose learning abilities are much poorer (12).

The neuroprotective effect according to formula I to protect may be assessed using-the gerbil global ischemia model and such a protocol:

1—Method
* Surgery
Anesthesia with isoflurane (0.5-4%).
The common carotid arteries (left and right) are freed from tissue.
Occlusion of the arteries using Bulldog microclamps during 5 min.
Removal of clamps (reperfusion)
Stabulation of the animals under heating lamp until awake.
Stabulation of the animals in the animalry in individual cages.
* Sacrifice of the animals
7 days after ischemia (Decapitation or overdose of pentobarbital).
Sampling of the brain.
* Histological parameters
Freezing of the brain in isopentane (−20° C.)
Slicing of the hippocampus using a cryo-microtome (20 μm).

Staining with cresyl violet method

Evaluation of the lesions (in CA1/CA2 subfields of the hippocampus) by a modified Gerhard & Boast score (13).

2—Treatment

Administration (ip) of the compound according to formula I or the vehicle: 15 min, 24 hours and 48 hours after reperfusion (5-10 min after the recovery of the anesthesia).

Standard protocol

A total of 40 animals is employed; said animals are divided into 5 groups of 8 animals:

Group A: control (saline)

Groups B-D: test compound is administered at 3 different doses (10 mg/kg; 20 mg/kg, 40 mg/kg);

Group E: reference compound (Orotic acid 3×300 mg/kg, ip).

For the test compound set out in Example 1 (i.e. 1,3-benzothiazol-2-yl[2-({4-[(4-methyl-piperazin-1-yl)methyl]-benzyl}oxy)pyrimidin-4-yl]acetonitrile) used in the above described assay at a concentration of 40 mg per kg, an inhibition of neuronal death of about 60% is determined.

c) Assessment of the BBB Passage: Brain and Plasma Sampling

The compounds of the present invention are useful in the treatment and/or prophylaxis of cerebral ischemic disorders or CNS disorders. Specifically, the compounds of the present invention show a good capacity to cross the blood-brain barrier (EBB). The BBB passing capacity of the compounds according to formulae I or II may be assessed using the below protocols. The objective of this assay is to quantify the amount of the test compounds according to formulae I or II in the brain of rats following i.v. administration.

Six male Crl:CD(SD)Br Sprague Dawley rats (about 8 weeks old and having a weight of about 300 g) were divided into the 3 following groups:

Group 1

2 animals for i.v. administration (10 mg/kg of test compound of formula I in 0.9% NaCl for injection). The test compound is administered by single dose (dose regimen). The sampling is performed at 0.25 h after sacrifice.

Group 2

2 animals for i.v. administration (10 mg/kg of test compound of formula I in 0.9% NaCl for injection). The test compound is administered by single dose (dose regimen). The sampling is performed at 0.5 h after sacrifice.

Group 3

2 animals for i.v. administration (10 mg/kg of test compound of formula I in 0.9% NaCl for injection). The test compound is administered by single dose (dose regimen). The sampling is performed at 1 h after sacrifice.

At each scheduled killing time, the animals of the corresponding group are deeply anaesthetised with diethyl ether. The blood for the corresponding blood samples is collected into heparinised tubes and centrifuged to remove the blood cells thus providing plasma. Plasma samples obtained at each sampling time (i.e. at t=0.25 h, 0.5 h, 1 h) from the rats of each group after administration of the test compound of formula (I) are pooled in order to obtain 1 pooled sample per sampling time per group. Rats are then sacrificed by exsanguination.

For the-brain sampling, the whole brain (cerebrum and cerebellum) of the sacrificed animals is removed. Brain from two animals per sampling time (i.e. at t=0.25 h, 0.5 h, 1 h after administration) are pooled in order to obtain one pooled sample per sampling time. Each pooled sample is homogenized in a solvent mixture (acetonitrile/methanol/dimethyl-sulfoxide, 50:48:2 by volume) centrifuged and the supernatant analyzed for the test compound.

Concentrations in plasma samples and brain homogenates are quantified according to an analytical HPLC-MS/MS method, properly developed for the compound.

The test compound used in this assay is the one set out in Example 1 (i.e. 1,3-benzothiazol-2-yl[2-({4-[(4-methylpiperazin-1-yl)methyl]-benzyl}oxy)pyrimidin-4-yl]acetonitrile.

The concentrations of the test compound in plasma and brain homogenate samples. assayed by HPLC-MS/MS are illustrated in the below Table 1.

TABLE 1

Plasma and brain concentrations of the test compound (as Tri-TFA salt) found after intravenous administration at the dose of 10 mg/kg.

| Time (h) | Pooled Samples (n = 2) | | |
|---|---|---|---|
| | Plasma ng/ml | Brain ng/g | Brain/Plasma ratio |
| 0.25 | 2835 | 919 | 0.32 |
| 0.5 | 2158 | 657 | 0.30 |
| 1 | 1983 | 679 | 0.34 |

From Table 1, a considerable and sustained passage of the test compound into the brain may be seen.

REFERENCES

1. Davis, Roger J., Signal Transduction by the JNK Group of MAP Kinases. *Cell*, 2000, 103: 239-252.
2. Gupta, S. et al., Selective interaction of JNK protein kinase isoforms with transcription factors. *The EMBO Journal*, 1996, 158(11): 2760-2770.
3. Dumitru, Calin D. et al. TNF-alpha induction by LPS is regulated posttranscriptionally via a Tpl2/ERK-dependent pathway. *Cell* 2000, 103: 1071-1083.
4. Han, Z. et al., C-Jun N-terminal kinase is required for metalloproteinase expression and joint destruction in inflammatory arthritis. *The Journal of Clinical Investigation* 2001, 108 (1):73-81.
5. Nishina, H., et al. Impaired CD28-mediated interleukin 2 production and proliferation in stress kinase SAPK/ERK1 kinase (SEK1)/rnitogen-activated protein kinase kinase 4 (MKK4)-deficient T lymphocytes. *Journal of Experimental Medicine* 1997, 186(6): 941-953.
6. Kempiak, Stephan J. et al. The Jun Kinase Cascade is responsible for activating the CD28 Response element of the IL-2 Promoter: proof of cross-talk with the IKB Kinase Cascade, *The Journal of Immunology*, 1999, 162: 3176-3187.
7. De la Monte, S. M. et al., Oxygen free radical injury is sufficient to cause some Alzheimer-type molecular abnormalities in human CNS neuronal cells. *J. Alzheimer's Dis.* 2000, 2(3-4):261-281.
8. Zhu, X, Activation and redistribution of c-Jun N-terminal kinase/stress activated protein kinase in degenerating neurons in Alzheimer's disease, *Journal of Neurochemistry* 2001, 76: 435-441
9. Xu, L. et al., Assess the in-vivo activation of signal transduction pathways with Pathdetect® reporting systems, *Strategies* 2001, 14 (1): 17-19.
10. Guha, M. and Mackinan, N., LPS induction of gene expression in human monocytes, *Cellular Signalling* 2001, 13: 85-94.

11. Hunter J. L. et al, Animal models of acute ischemic stroke: can they predict clinically successful neuroprotective drugs? *TIPS* 1995, 16:123-128.
12. Block, F., Global Ischemia And Behavioural Deficits, *Progress in Neurobiology* 1999, 58: 279-295.
13. Gerhard S C and Boast C A, *Behavioral Neuroscience* 1988, 102: 301-303.
14. Betz et. al, 1994. Blood-Brain-Cerebrospinal Fluid Barriers. Chapter 32 in Basic Neurochemistry (5th Edition, Eds Siegel, Albers, Agranoff, Molinoff), pp 681-701.
15. Goldstein and Betz, 1986. The Blood-Brain Barrier. Scientific American, September, 1986, pp 74-83.
16. WO 01/47920

The invention claimed is:

1. A piperazine benzothiazole compound having formula I

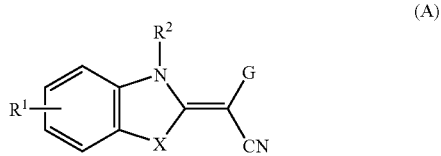

(A)

as well as its tautomers, its geometrical isomers, its optically active forms as an enantiomer, a diastereomer and as a racemate, as well as pharmaceutically acceptable salts thereof, wherein R is selected from the group comprising or consisting of hydrogen, $C_1$-$C_6$-alkyl, $C_1$-$C_6$-alkyl aryl, heteroaryl, $C_1$-$C_6$-alkyl heteroaryl, $C_2$-$C_6$-alkenyl, $C_2$-$C_6$-alkenyl aryl, $C_2$-$C_6$-alkenyl heteroaryl, $C_2$-$C_6$-alkynyl, $C_2$-$C_6$-alkynyl aryl, $C_2$-$C_6$-alkynyl heteroaryl, $C_3$-$C_8$-cycloalkyl, heterocycloalkyl, $C_1$-$C_6$-alkyl cycloalkyl, $C_1$-$C_6$-alkyl heterocycloalkyl, $C_1$-$C_6$-alkyl carboxy, acyl, $C_1$-$C_6$-alkyl acyl, acyloxy, $C_1$-$C_6$-alkyl acyloxy, $C_1$-$C_6$-alkyl alkoxy, alkoxycarbonyl, $C_1$-$C_6$-alkyl alkoxycarbonyl, aminocarbonyl, $C_1$-$C_6$-alkyl aminocarbonyl, acylamino, $C_1$-$C_6$-alkyl acylamino, ureido, $C_1$-$C_6$-alkyl ureido, amino, $C_1$-$C_6$-alkyl amino, sulfonyloxy, $C_1$-$C_6$-alkyl sulfonyloxy, sulfonyl, $C_1$-$C_6$-alkyl sulfonyl, sulfinyl, $C_1$-$C_6$-alkyl sulfinyl, sulfanyl, $C_1$-$C_6$-alkyl sulfanyl, sulfonylamino, and $C_1$-$C_6$-alkyl sulfonylamino;

$R^1$ is selected from the group comprising or consisting of H, halogen, cyano, nitro, amino, $C_1$-$C_6$-alkyl, $C_2$-$C_6$-alkenyl, $C_2$-$C_6$-alkynyl, $C_1$-$C_6$-alkyl-aryl, aryl or heteroaryl, $C_1$-$C_6$-alkyl-heteroaryl, -C(O)-$OR^2$, -C(O)-$R^2$, -C(O)-$NR^2R^{2'}$, and -($SO_2$)$R^2$, with $R^2$ and $R^{2'}$ being independently selected from the group consisting of hydrogen, $C_1$-$C_6$ alkyl, $C_2$-$C_6$ alkenyl, $C_2$-$C_6$ alkynyl, aryl, heteroaryl, $C_1$-$C_6$-alkyl aryl, $C_1C_6$-alkyl heteroaryl and combinations mixtures thereof; and n is an integer from 0 to 3.

2. The piperazine benzothiazole compound according to claim 1, wherein $R^1$ is hydrogen.

3. The piperazine benzothiazole compound according to claim 1, wherein R is selected from the group consisting of hydrogen, $C_1$-$C_3$ alkyl, aminocarbonyl, $C_1$-$C_6$-alkyl alkoxycarbonyl, $C_1$-$C_6$-alkyl alkoxy, $C_1$-$C_6$-alkyl acyloxy, alkoxycarbonyl, and $C_1$-$C_6$-alkyl aminocarbonyl.

4. The piperazine benzothiazole compound according to claim 3, wherein R is H, or $C_1$-$C_3$ alkyl, in particular a methyl or an ethyl moiety, or $C_1$-$C_6$-alkyl alkoxy.

5. The piperazine benzothiazole compound according to claim 1, wherein n is 1.

6. The piperazine benzothiazole compound according to claim 1 selected from the group consisting of:

1,3-benzothiazol-2-yl[2-({4-[(4-methylpiperazin-1-yl)methyl]benzyl}oxy)pyrimidin-4-yl]acetonitrile,
1,3-benzothiazol-2-yl[2-({4-[(4-benzyl-piperazin-1-yl)methyl]-benzyl}oxy)pyrimidin-4-yl]acetonitrile,
1,3-benzothiazol-2-yl(2-{[4-(piperazin-1-ylmethyl)benzyl]oxy}pyrimidin-4-yl)acetonitrile,
1,3-benzothiazol-2-yl[2-({4-[(4-formylpiperazin-1-yl)methyl]benzyl}oxy)pyrimidin-4-yl]acetonitrile,
[2-({4-[(4-acetylpiperazin-1-yl)methyl]benzyl}oxy)pyrimidin-4-yl](1,3-benzothiazol-2-yl)acetonitrile,
(3H-Benzothiazol-2-ylidene)-{2-[4-(4-[1,2,4]oxadiazol-3-ylmethyl-piperazin-1-ylmethyl)-benzyloxy]-pyrimidin-4-yl}-acetonitrile,
4-(4-{4-[(3H-Benzothiazol-2-ylidene)-cyano-methyl]-pyrimidin-2-yloxymethyl}-benzyl)-piperazine-1-carboxylic acid methyl ester,
2-[4-(4-{4-[(3H-Benzothiazol-2-ylidene)-cyano-methyl]-pyrimidin-2-yloxymethyl}-benzyl)-piperazin-1-yl]-acetamide,
(2-{4-[4-(2-Amino-acetyl)-piperazin-1-ylmethyl]-benzyloxy}-pyrimidin-4-yl)-(3H-benzothiazol-2-ylidene)-acetonitrile,
[4-(4-{4-[(3H-Benzothiazol-2-ylidene)-cyano-methyl]-pyrimidin-2-yloxymethyl}-benzyl)-piperazin-1-yl]-acetic acid methyl ester,
(3H-Benzothiazol-2-ylidene)-(2-{4-[4-(2-methoxy-ethyl)-piperazin-1-ylmethyl]-benzyloxy}-pyrimidin-4-yl)-acetonitrile,
4-(4-{4-[(3H-Benzothiazol-2-ylidene)-cyano-methyl]-pyrimidin-2-yloxymethyl}-benzyl)-piperazine-1-carboxylic acid dimethylamide,
(3H-Benzothiazol-2-ylidene)-{2-[4-(4-ethyl-piperazin-1-ylmethyl)-benzyloxy]-pyrimidin-4-yl}-acetonitrile, and
(3H-Benzothiazol-2-ylidene)-(2-{4-[4-(2-hydroxy-ethyl)-piperazin-1-ylmethyl]-benzyloxy}-pyrimidin-4-yl)-acetonitrile.

7. A pharmaceutical composition, comprising:
a therapeutically effective amount of the piperazine benzothiazole compound according to claim 1 with a pharmaceutically acceptable carrier.

8. A method of treating ischemia, comprising:
administering a therapeutically effective amount of the pharmaceutical composition according to claim 7 to a subject in need of treatment for ischemia.

9. A process for the preparation of a piperazine benzothiazole compound claimed in claim 1, comprising:
reacting a pyrimidinylbenzothiazole compound of formula (IV)

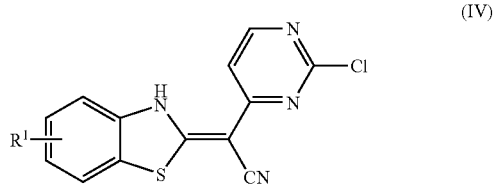

(IV)

with a piperazinyl alcohol compound of formula (V)

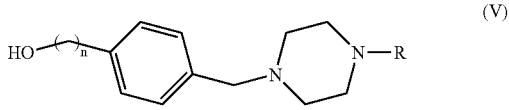

(V)

wherein R, $R^1$ and n are as defined in claim 1, thereby preparing the piperazine benzothiazole compound of claim 1.

* * * * *